(12) United States Patent
Kim et al.

(10) Patent No.: US 11,185,608 B2
(45) Date of Patent: Nov. 30, 2021

(54) METHOD OF TREATING A SUPERELASTIC MEDICAL DEVICE TO IMPROVE FATIGUE LIFE

(71) Applicant: Cook Medical Technologies LLC, Bloomington, IN (US)

(72) Inventors: Seoggwan Kim, West Lafayette, IN (US); Tony Trudnowski, West Lafayette, IN (US); Nolan Xanh, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 776 days.

(21) Appl. No.: 16/059,228

(22) Filed: Aug. 9, 2018

(65) Prior Publication Data

US 2020/0046878 A1 Feb. 13, 2020

(51) Int. Cl.
| | |
|---|---|
| *C22F 1/10* | (2006.01) |
| *A61L 27/06* | (2006.01) |
| *A61L 31/02* | (2006.01) |
| *C22F 1/00* | (2006.01) |
| *A61L 31/14* | (2006.01) |
| *A61B 17/00* | (2006.01) |

(52) U.S. Cl.
CPC .......... *A61L 27/06* (2013.01); *A61L 31/022* (2013.01); *C22F 1/006* (2013.01); *A61B 2017/00526* (2013.01); *A61B 2017/00867* (2013.01); *A61L 31/14* (2013.01); *A61L 2400/16* (2013.01); *C21D 2201/01* (2013.01)

(58) Field of Classification Search
None
See application file for complete search history.

(56) References Cited

U.S. PATENT DOCUMENTS

| 4,412,872 A | * | 11/1983 | Albrecht | ................. C22F 1/006 |
| | | | | 148/402 |
| 7,789,979 B2 | | 9/2010 | Dooley et al. | |
| 7,811,393 B2 | | 10/2010 | Dooley et al. | |

(Continued)

OTHER PUBLICATIONS

Gupta, S., et al., "High Compressive Pre-Strains Reduce the Bending Fatigue Life of Nitinol Wire," *J. Mech. Behav. Biomed Matter*, 44, Apr. 2015, pp. 96-108 (Abstract only).

(Continued)

*Primary Examiner* — George Wyszomierski
(74) *Attorney, Agent, or Firm* — Crowell & Moring LLP

(57) ABSTRACT

A method of improving the fatigue life of a superelastic medical device includes applying a compressive stress to a fatigue critical location of a medical device comprising a superelastic nickel-titanium alloy, where the compressive stress induces a compressive strain of greater than 9% in the fatigue critical location. After inducing the compressive strain, the compressive stress is released. A tensile stress is applied to the fatigue critical location of the medical device, where the tensile stress induces a tensile strain of greater than 9% in the fatigue critical location. After inducing the tensile strain, the tensile stress is released. After application and release of each of the compressive stress and the tensile stress, the fatigue critical location includes a non-zero amount of residual strain, and the medical device may exhibit improved fatigue properties.

20 Claims, 6 Drawing Sheets

(56) References Cited

U.S. PATENT DOCUMENTS

| | | |
|---|---|---|
| 8,177,927 B2 | 5/2012 | Dooley et al. |
| 8,216,396 B2 | 7/2012 | Dooley et al. |
| 8,709,177 B2 | 4/2014 | Dooley et al. |
| 2016/0123471 A1* | 5/2016 | Roy .................... E21B 33/1212 277/336 |

OTHER PUBLICATIONS

Ong, I., et al., "Effect of Pre-Strain on Nitinol Fatigue Life", *SMST 2015, Shape Memory and Superelastic Technologies Conference and Exhibition*, Chipping Norton, Oxfordshire, UK, May 18-22, 2015 (20 pp.).

Senthilnathan, K., et al., "Effect of Tensile and Compressive Pre-Strains on Superelastic Diamond Surrogates", *SMST 2017, Shape Memory and Superelastic Technologies Conference and Exposition*, San Diego, CA, May 15-19, 2017 (44 pages).

\* cited by examiner

METHOD OF TREATING A SUPERELASTIC MEDICAL DEVICE TO IMPROVE FATIGUE LIFE

TECHNICAL FIELD

The present disclosure is related generally to medical devices and more particularly to a method of treating a superelastic medical device to improve fatigue life.

BACKGROUND

The insertion or implantation of intraluminal medical devices may provide an alternative to conventional invasive surgery for treatment of a range of ailments of the vascular system and biliary tract. Nickel-titanium alloys are commonly used for the manufacture of intraluminal medical devices, such as self-expandable stents, stent grafts, embolic protection filters, and stone extraction baskets. Such devices may exploit the superelastic or shape memory behavior of equiatomic or near-equiatomic nickel-titanium alloys (which may be referred to as "Nitinol" or "Nitinol alloys") to deploy from a small-diameter delivery configuration to a deployed configuration in a body vessel.

In use in the body, intraluminal medical devices may be subjected to high stresses and high cyclic loading due to exposure to alternating loads from vessel movement and changes in pressure. Thus, fatigue failure of intraluminal devices can be common and problematic.

Nitinol medical devices are known to have a fatigue endurance limit of 0.4% to 0.6% (strain amplitude). Testing of the Zilver Vena™ stent, which comprises a superelastic nickel-titanium alloy, reveals a similar fatigue endurance limit, as shown by the data of FIG. 1A. It would be advantageous to improve the fatigue properties of Nitinol medical devices for more reliable performance in vivo. A number of investigations have indicated that pre-straining of Nitinol devices in tension can lead to an improvement in fatigue life.

BRIEF SUMMARY

A method of improving the fatigue life of a superelastic medical device includes applying a compressive stress to a fatigue critical location of a medical device comprising a superelastic nickel-titanium alloy, where the compressive stress induces a compressive strain of greater than 9% in the fatigue critical location. After inducing the compressive strain, the compressive stress is released. A tensile stress is applied to the fatigue critical location of the medical device, where the tensile stress induces a tensile strain of greater than 9% in the fatigue critical location. After inducing the tensile strain, the tensile stress is released. After application and release of each of the compressive stress and the tensile stress, the fatigue critical location includes a non-zero amount of residual strain, and the medical device may exhibit improved fatigue properties. The compressive stress may be applied before or after the tensile stress is applied.

BRIEF DESCRIPTION OF THE DRAWINGS

FIG. 5B also shows an example of deforming a medical device so as to apply a compressive stress to a fatigue critical location.

DETAILED DESCRIPTION

Described herein is new method of treating a medical device comprising a superelastic nickel-titanium alloy to improve the fatigue properties of the device. Testing indicates that the fatigue endurance limit of a stent treated according to the disclosed method may be increased by over 115% compared to an untreated stent.

Figure 2:
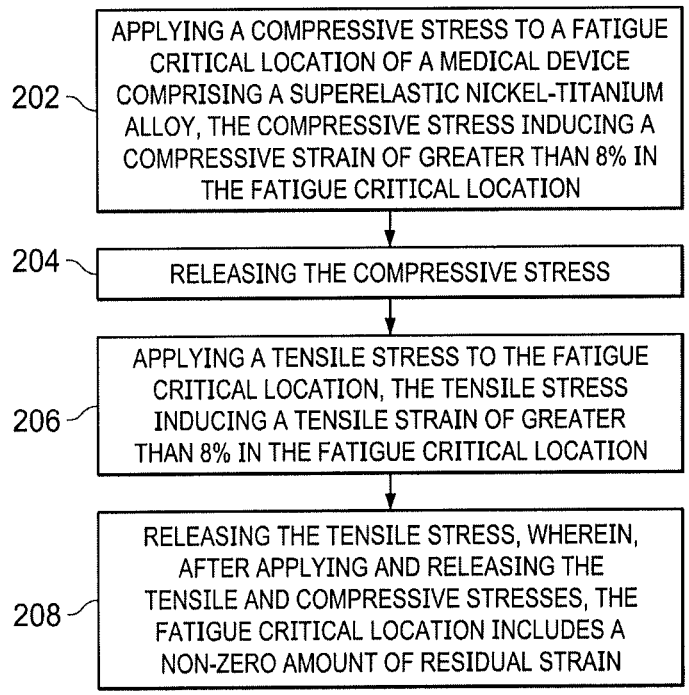
FIG. 2 is a flow chart showing one embodiment of the treatment method.

Referring to the flow chart of FIG. 2, the treatment method includes, according to one embodiment, applying 202 a compressive stress to a fatigue critical location of a medical device comprising a superelastic nickel-titanium alloy. The compressive stress induces a compressive strain of greater than 9%, at least about 10%, or at least about 11% in the fatigue critical location. The amount of compressive strain is selected to exceed the elastic recovery limit of the superelastic nickel-titanium alloy, as explained below, and may be as high as about 15%. Typically, the compressive strain is in a range from greater than 9% to about 12%, or from about 10% to about 11%. After inducing the desired amount of compressive strain, the compressive stress is released 204.

A tensile stress is then applied 206 to the fatigue critical location of the medical device. The tensile stress induces a tensile strain of greater than 9%, at least about 10%, or at least about 11% in the fatigue critical location. The amount of tensile strain is also selected to exceed the elastic recovery limit of the superelastic nickel-titanium alloy, and may be as high as about 15%. Typically, the tensile strain is in a range from greater than 9% to about 12%, or from about 10% to about 11%. After inducing the desired amount of tensile strain, the tensile stress is released 208.

After application and release of each of the compressive stress and the tensile stress, the fatigue critical location includes a non-zero amount of residual strain and may also exhibit changes in material properties. The amount of residual strain may be determined by the magnitude of the tensile and compressive stresses described above, which induce tensile and compressive strains beyond the elastic recovery limit. The residual strain may alternatively be referred to as plastic deformation or non-recoverable strain. The fatigue critical location may also include some amount of residual stress after the applied compressive and tensile stresses are released.

As shown in the flow chart of FIG. 2, the compressive stress may be applied before the tensile stress. Alternatively, as shown in the flow chart of FIG. 3, the tensile stress may be applied before the compressive stress.

Figure 3:
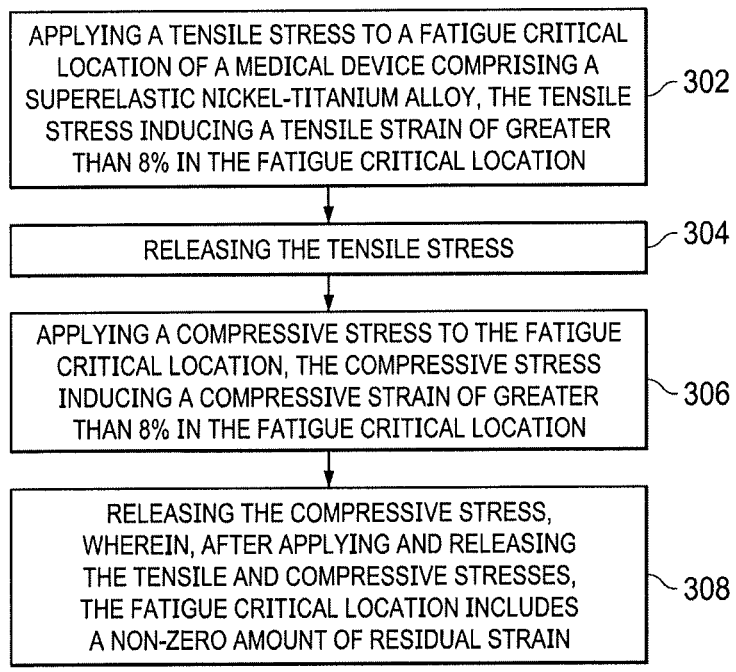
FIG. 3 is a flow chart showing one embodiment of the treatment method.

Referring to FIG. 3, the treatment method includes, according to another embodiment, applying 302 a tensile stress to a fatigue critical location of a medical device comprising a superelastic nickel-titanium alloy. The tensile stress induces a tensile strain of greater than 9%, at least about 10%, or at least about 11%. The amount of tensile strain is selected to exceed the elastic recovery limit of the superelastic nickel-titanium alloy, as explained below, and may be as high as about 15%. Typically, the tensile strain is in a range from greater than 9% to about 12%, or from about 10% to about 11%. After inducing the desired amount of tensile strain, the tensile stress is released 304.

A compressive stress is then applied 306 to the fatigue critical location of the medical device. The compressive stress induces a compressive strain of greater than 9%, at least about 10%, or at least about 11%. The amount of compressive strain is also selected to exceed the elastic recovery limit of the superelastic nickel-titanium alloy, and may be as high as about 15%. Typically, the compressive strain is in a range from greater than 9% to about 12%, or from about 10% to about 11%. After inducing the desired amount of compressive strain, the compressive stress is released 308. After application and release of each of the tensile stress and the compressive stress, the fatigue critical location includes a non-zero amount of residual strain and may also include changes in material properties, as mentioned above. In addition, there may be some amount of residual stress in the fatigue critical location after the applied compressive and tensile stresses are released.

The tensile stress and the compressive stress may be applied by radially compressing, radially expanding, bending, twisting, axially extending, axially compressing and/or otherwise deforming the medical device from an undeformed shape to a deformed shape. The application of the tensile and compressive stresses may be carried out manually or automatically using, for example, a programmable device capable of motion in one-, two-, or three-dimension(s). The amount of compressive and/or tensile strain induced in the fatigue critical location may be determined or predicted by computer simulations (e.g., finite element analysis (FEA). The application of the tensile and compressive stresses may be carried out under ambient conditions (e.g., at room temperature and/or at atmospheric pressure) for any suitable time duration, which may be on the order of seconds, minutes or hours. It is understood that the configuration of the medical device when no stress is applied (e.g., prior to application of the tensile stress and/or prior to application of the compressive stress) may be referred to as the "undeformed shape" of the medical device.

Figure 4A:
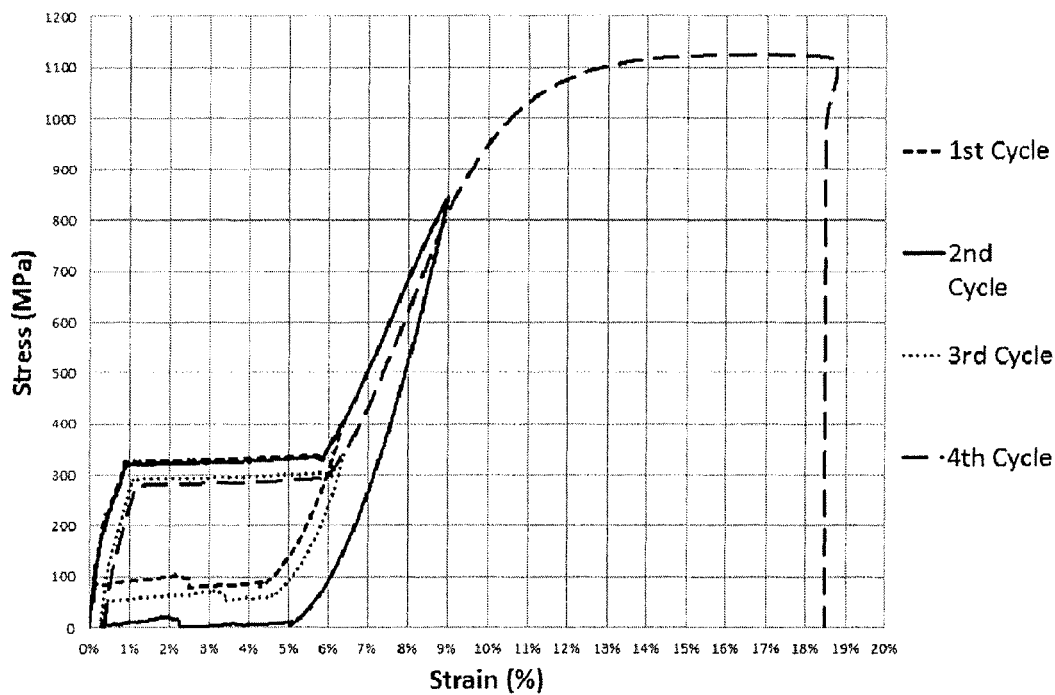
FIGS. 4A and 4B are stress-strain plots from a nickel-titanium alloy cannula showing different material behavior in response to different amounts of induced tensile strains.
Figure 4B:
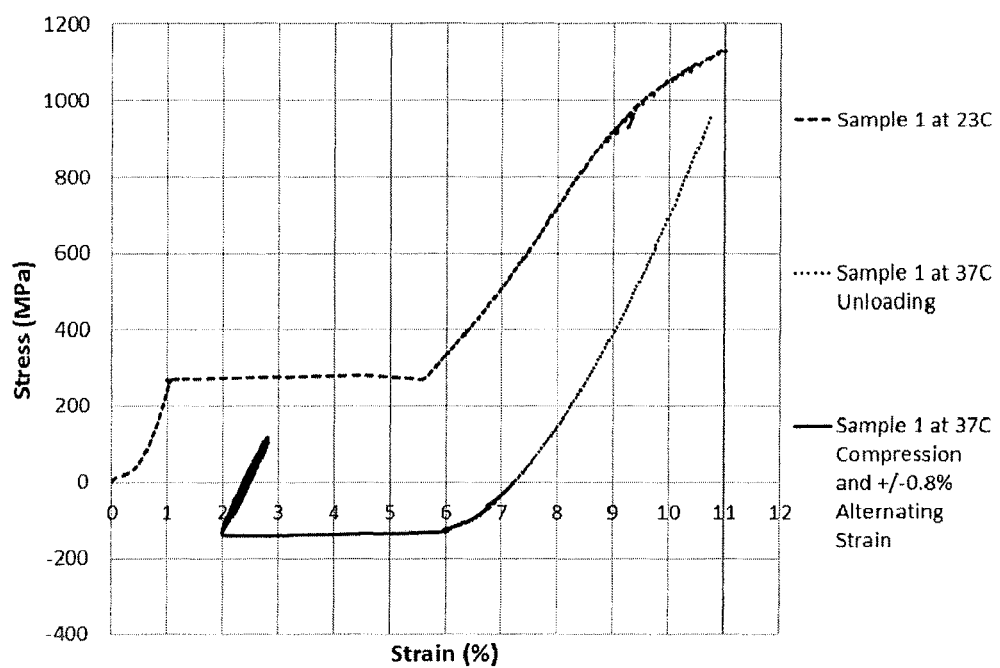

It is recognized that a non-zero amount of residual strain is present after the compressive and tensile stresses are released. The amount of the residual strain depends on the magnitude of the applied stresses applied along with the amount of strain that can be recovered by the superelastic nickel-titanium alloy. It is believed that, for the compressive and tensile stresses applied in this method, the amount of residual strain may lie in a range from about 0.3% to about 7%, and is preferably at least about 1%, or at least about 2%, and as high as about 6% or 7%. Higher amounts of residual strain may change the material properties of the fatigue critical location from superelastic to elastic-plastic, as indicated in FIGS. 4A and 4B, which may help to improve fatigue life. These figures show results of axial tensile tests on a nickel-titanium alloy cannula that illustrate the change in material properties possible at higher levels of applied tensile strain (and consequently, at higher levels of residual strain after the tensile stress is released). In FIG. 4A the cannula is exposed to 9% tensile strain and exhibits superelastic behavior upon release of the applied tensile stress, with a small amount (e.g., about 0.3%) of residual strain. In FIG. 4B, the cannula is exposed to 11% tensile strain and exhibits elastic-plastic behavior upon release of the applied tensile stress, resulting in a much higher amount (e.g., about 7%) of residual strain.

Superelastic nickel-titanium alloys, which may be referred to as Nitinol or Nitinol alloys, can "remember" and elastically recover a previous shape when an applied stress is removed. The elastic springback of superelastic nickel-titanium alloys is powered by a phase transformation from martensite to austenite, during which strains of up to about 8% (typically) may be recovered. The amount of strain that is recoverable by a superelastic nickel-titanium alloy may be referred to as the "elastic recovery limit" of the alloy. As would be recognized by the skilled artisan, a superelastic nickel-titanium alloy behaves superelastically at temperatures at which the austenite phase is stable, i.e., at temperatures at least above the austenite start temperature ($A_s$) of the nickel-titanium alloy, and preferably above the austenite final temperature ($A_f$) of the alloy. The $A_s$ is the temperature at which a phase transformation to austenite begins upon heating for a nickel-titanium alloy exhibiting a martensite-to-austenite transformation, and $A_f$ is the temperature at which the phase transformation to austenite concludes upon heating.

Slightly nickel-rich Nitinol alloys that include greater than 50 at. % Ni and less than 50 at. % Ti are known to behave superelastically at body temperature and thus may be useful for stents and other medical devices. For example, nickel-titanium alloys including 50.6-50.8 at. % Ni and 49.2-49.4 at. % Ti are known to be medical grade Nitinol alloys. Generally speaking, the superelastic nickel-titanium alloy used herein may include from greater than 50 at. % to about 55 at. % nickel and from about 45 at. % to less than 50 at. % titanium. The superelastic nickel-titanium alloy may also include one or more additional alloying elements, such as transition metals or other elements, such as boron (B). For example, one or more of B, Al, Cr, Mn, Fe, Co, Cu, Zn, Ga, Ge, Zr, Nb, Mo, Tc, Ru, Rh, Pd, Ag, Cd, In, Sn, Sb, Hf, Ta, W, Re, Ir, Pt, Au, Hg, Tl, Pb, Bi, V, and Mischmetal may be included as the additional alloying element. Preferably, the superelastic nickel-titanium alloy is biocompatible. The $A_f$ of the superelastic nickel-titanium alloy may be less than body temperature (i.e., less than about 37° C.), and may also be less than room temperature (i.e., less than about 23° C.).

The fatigue critical location is typically on a surface of the medical device. It is understood that there may be more than one fatigue critical location on the medical device; thus, the description herein referring to "a fatigue critical location" or "the fatigue critical location" is understood to refer to any or all of the fatigue critical locations on the device. The fatigue critical location may be subjected to repeated (e.g., cyclic) stresses while the medical device is in use. Since exposure to repetitive stresses can lead to fatigue cracking and ultimately to failure of the medical device, it is beneficial to treat the medical device as set forth herein to effectively strengthen the fatigue critical location. Other portions of the medical device, such as sub-surface regions and surface locations not subjected to repetitive stresses, may not be strained during the treatment method to the same degree as the fatigue critical location. More specifically, when the fatigue critical location is subjected to the compressive and tensile stresses described above, the sub-surface regions and surface locations not subjected to cyclic stresses in use may experience a smaller amount of strain that is within the elastic recovery limit of the superelastic nickel-titanium alloy.

The medical device may be any insertable and/or implantable medical device that benefits from increased fatigue resistance, such as a vascular device, a biliary device, or an orthopedic device. For example, the medical device may be an intraluminal device selected from the group consisting of: stent, filter, basket, plug, grasper, snare, and heart valve. All or a portion of the medical device (e.g., one or more components of the medical device) may comprise the superelastic nickel-titanium alloy.

Figure 1A:
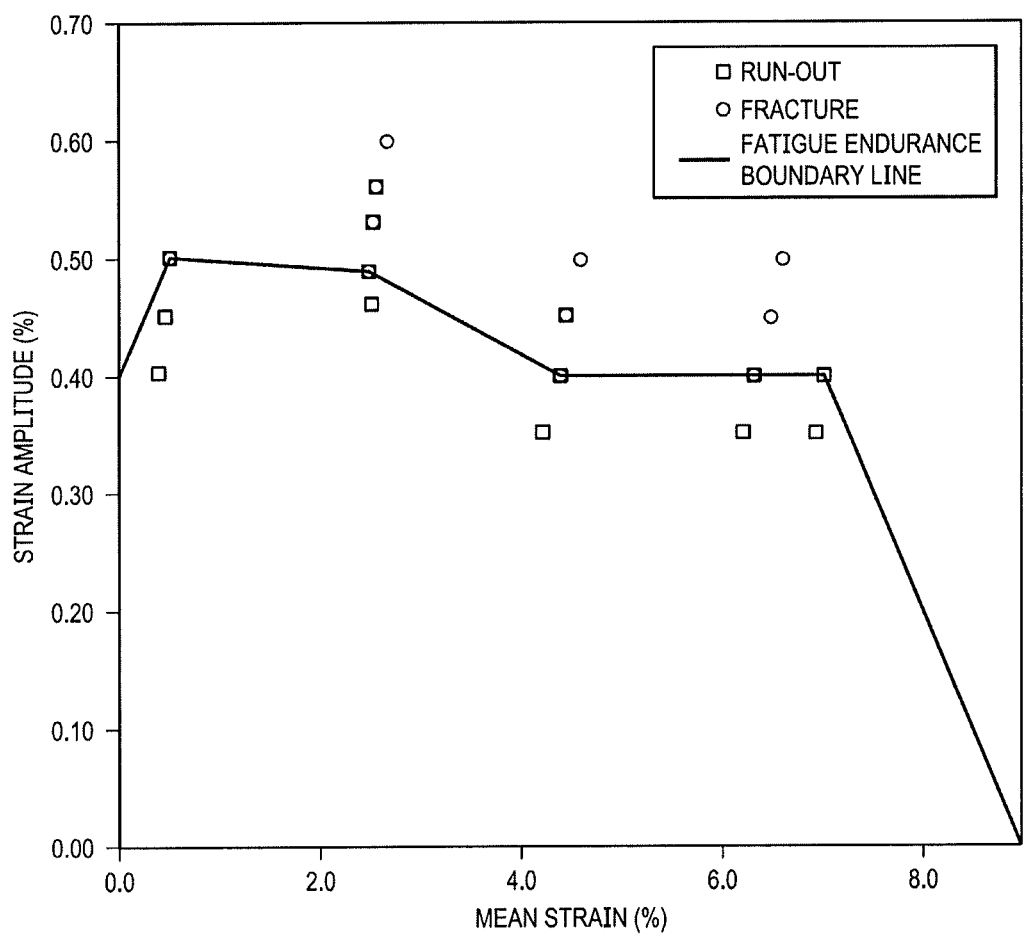
FIG. 1A shows strain amplitude (%) versus mean strain (%) for a Zilver Vena™ stent that has not been treated to improve fatigue life.
Figure 1B:
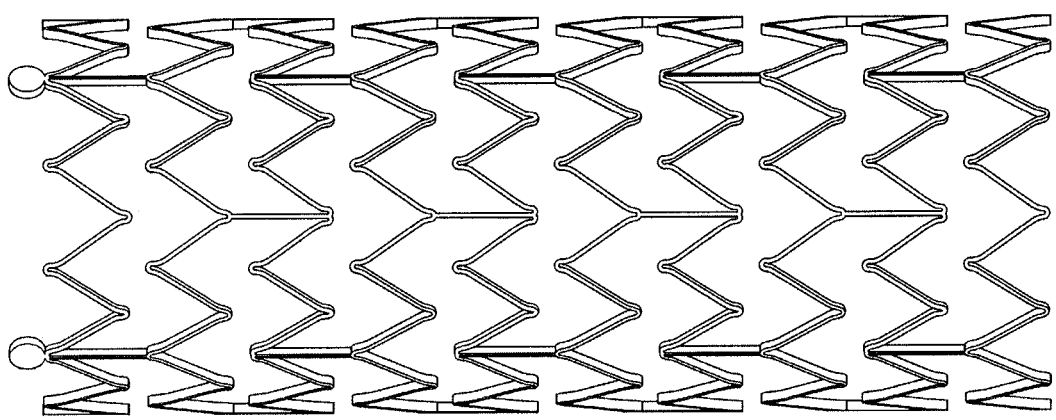
FIG. 1B shows the geometry of a portion of a Zilver Vena™ stent.
Figure 5A:
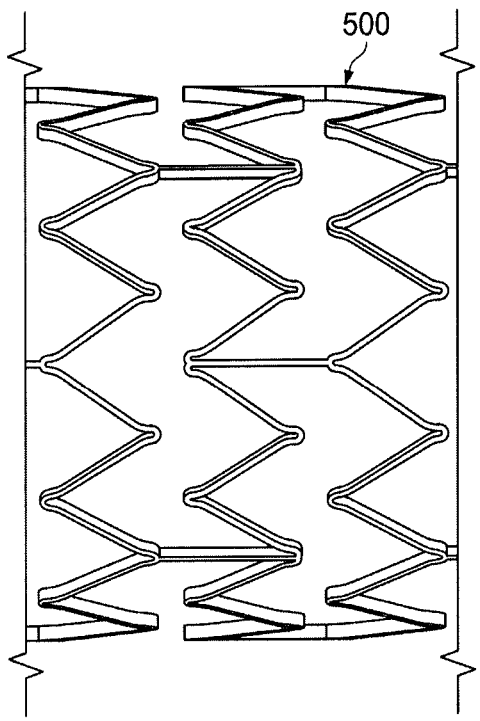
FIG. 5A illustrates a portion of an exemplary stent in a radially expanded configuration.
Figure 5B:
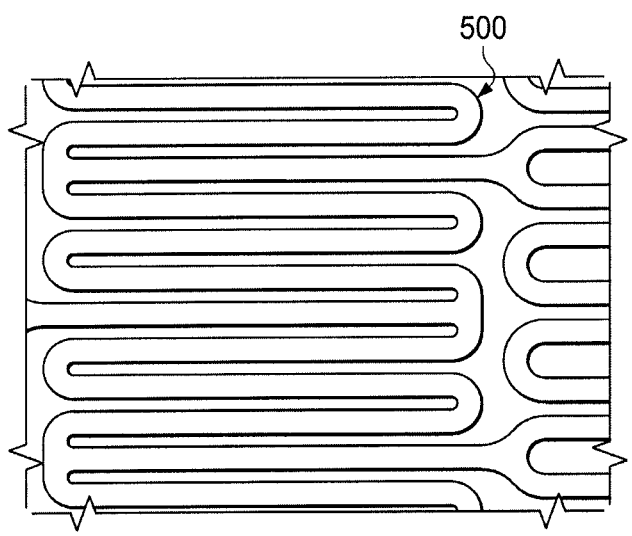
FIG. 5B illustrates a portion of an exemplary stent in a radially compressed configuration.

In one example, the intraluminal medical device may comprise a stent configured to expand from a radially compressed configuration for delivery into the body vessel to a radially expanded configuration for deployment at a treatment site in the vessel. The stent may comprise an arrangement of interconnected struts, as shown in FIG. 1B, which illustrates a portion of the Zilver Vena™ stent, where the interconnected struts comprise the superelastic nickel-titanium alloy. In FIG. 5A, a portion of an exemplary stent 500 is in a radially expanded configuration where the interconnected struts are extended and disposed at one or more angles with respect to the axial direction. In FIG. 5B, the exemplary stent 500 is in a radially compressed configuration where the interconnected struts are collapsed so as to be substantially aligned along an axial direction. The stent geometry shown in the figures is merely exemplary. Any arrangement of interconnected struts that may be laser-cut or otherwise carved out of a thin-walled tube may be suitable for the stent, provided that the stent provides sufficient radial support when expanded at the endoluminal treatment site. The stent may alternatively be composed of a cylindrical woven wire structure or another tubular configuration based on one or more wires that are formed to define the interconnected struts.

Figure 6:
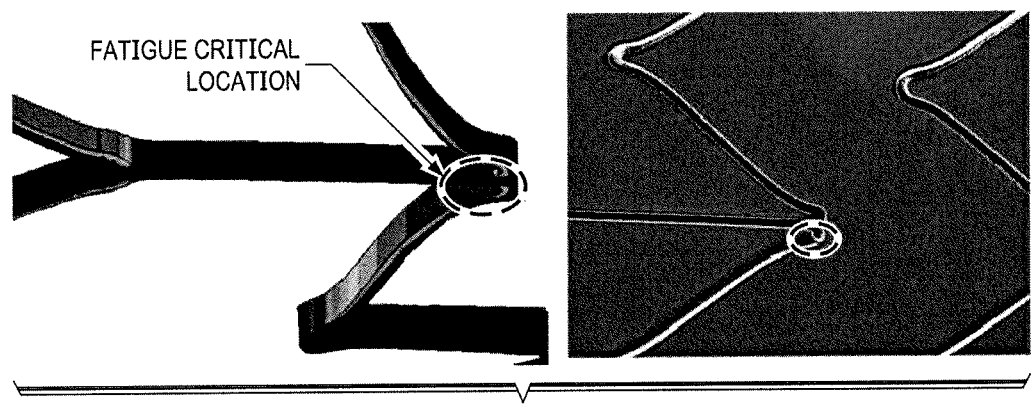
FIG. 6 shows a fatigue critical location on a surface of the exemplary stent between adjacent interconnected struts; the figure on the left is generated by finite element analysis (FEA) software, and the figure on the right is an optical image.

As can be seen in FIG. 6, the fatigue critical location may lie on a surface of the stent between adjacent interconnected struts.

Figure 7:
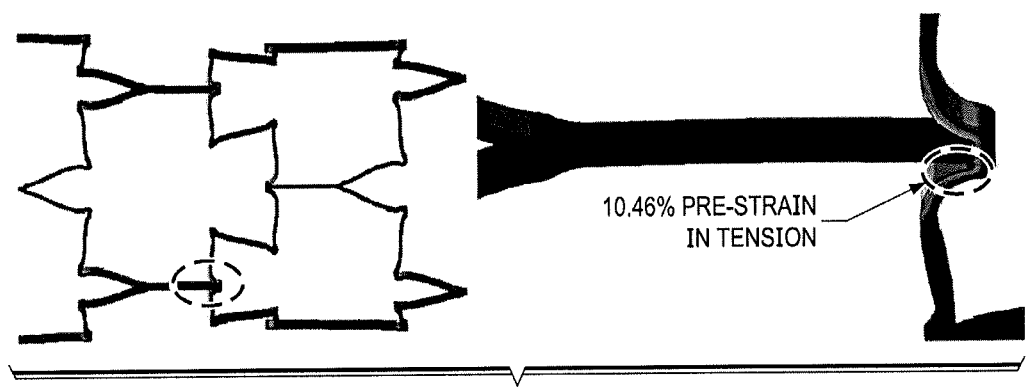
FIG. 7 shows an example of deforming a medical device so as to apply a tensile stress to the fatigue critical location. In this case, the tensile stress is applied by axially extending the stent shown in FIG. 5A, and a tensile strain in excess of 9% (about 10.5% in this example) is induced in the fatigue critical location. The images are generated by FEA software.

FIG. 7 shows an example of deforming the medical device so as to apply a tensile stress to the fatigue critical location. In this case, the tensile stress is applied by axially extending the stent, and a tensile strain in excess of 9% (about 10.5% in this example) is induced in the fatigue critical location. The schematics and strain values are obtained using FEA software, specifically, ABAQUS developed by Dassault Systemes. The geometry of the stent is modeled using elements and the material of the stent is characterized by testing. Three cells of the stent are chosen to be within the gauge length. Both ends of the stent are constrained except the axial degree of freedom of one end to apply axial displacement. During the FEA simulations, the stent is axially extended in tension to find the displacements to reach target mean and alternating strains. Those displacements are utilized for the actual benchtop fatigue testing of the stent.

By comparing the schematic of FIG. 7 with the schematic of FIG. 5A, the extent of axial extension of the stent can be appreciated. In practice, the axial extension may be achieved manually or, in another example, by placing the stent over a mandrel of a suitable diameter and extending one end of the stent in the axial direction while the other end of the stent remains stationary on the mandrel.

Figure 8:
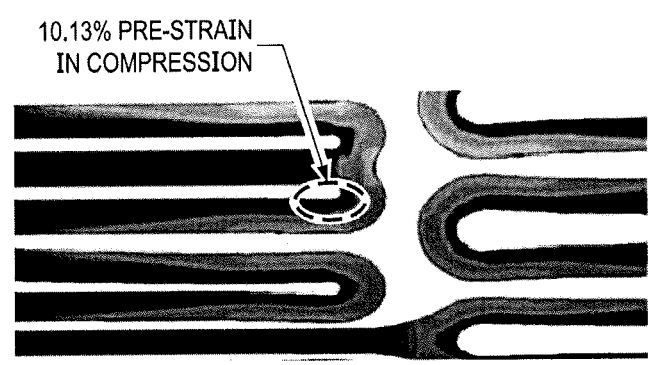
FIG. 8 shows an example of deforming a medical device so as to apply a compressive stress to the fatigue critical location. In this case, the compressive stress is applied by radially compressing the stent shown in FIG. 5A, and compressive strain in excess of 9% (about 10.1% in this example) is induced in the fatigue critical location. The images are generated by FEA software.

FIG. 8 shows an example of deforming the medical device so as to apply a compressive stress to the fatigue critical location. In this case, the stent is radially compressed, or crimped, such that a compressive strain in excess of 9% (about 10.1% in this example) is induced in the fatigue critical location. The schematic and strain values are obtained using FEA software, as described above. In practice, the radial compression may be carried out using a commercially available stent crimping apparatus, such as those available from Machine Solutions Inc. (MSI) of Flagstaff, Ariz.

As indicated above, the tensile stress may be applied prior to the compressive stress, or vice versa. It is understood that, during application of the applied tensile and compressive stresses, one fatigue critical location may experience a tensile strain while another fatigue critical location experiences a compressive strain. The application of the tensile and compressive stresses may be repeated one or more times; however, initial tests suggest there may not be any significant fatigue life improvement with repetitive application of the stresses, and low cycle fatigue to fracture could be induced.

It is contemplated that the treatment method may be carried out prior to insertion of the medical device into a delivery system (e.g., a sheath) for transfer into a body vessel. In this case, the tensile stress may be applied (e.g., by axially extending the stent) before the compressive stress is applied, and the compressive stress may entail radial compression or crimping, as illustrated for example in FIGS. 7 and 8. It is understood that each application of tensile or compressive stress induces a tensile or compressive strain of over 9% in the fatigue critical location. In this example, in which the stent undergoes crimping to apply a compressive strain to the fatigue critical location shown in FIG. 8, crimping may be followed by insertion of the stent into the sheath for delivery into a body vessel. As the skilled artisan would recognize and as indicated above, crimping may also be used to apply a tensile strain to a different fatigue critical location on the stent. The compressive (or tensile) stress may be released when the stent is deployed (e.g., by retracting the sheath) in the body vessel. Some amount of the compressive (or tensile) stress may also be released as the stent is transferred into the sheath after crimping.

Prior to carrying out the above-described method, the medical device may undergo a heat setting treatment to impart a remembered shape (e.g., a radially expanded configuration) to the medical device and ensure the superelastic nickel-titanium alloy is fully austenitic at body temperature. Typically, heat setting is carried out at a temperature between about 350° C. and about 550° C. for a time duration of about 5-60 min. As noted above, it is preferred that the austenite start and finish temperatures ($A_s$ and $A_f$) are less than body temperature (i.e., less than 37° C.), and they may also be less than room temperature (e.g., about 25° C. or less). For example, an initial value of $A_f$ may lie between −15° C. and 25° C.

Figure 9A:
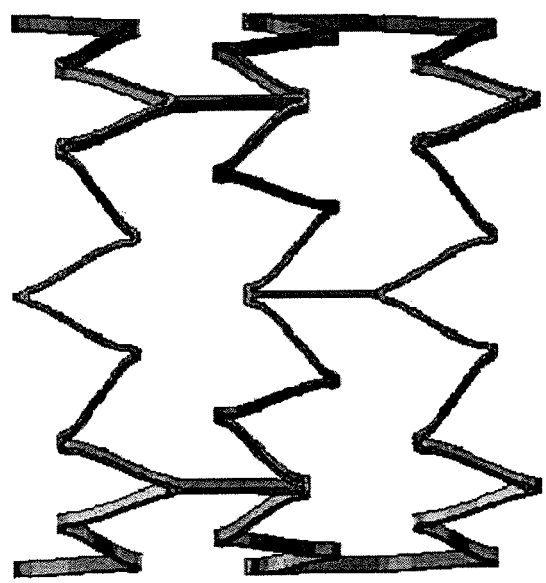
FIGS. 9A and 9B are schematics produced by FEA software that show the cyclic axial displacements experienced by the stent of FIG. 4A during axial tension-tension cyclic fatigue tests.
Figure 9B:
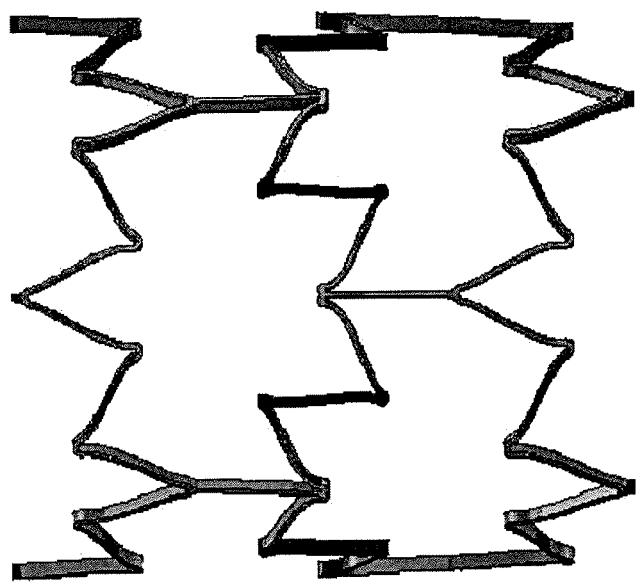

Medical devices that undergo the treatment method described in this disclosure may exhibit improved fatigue properties, as revealed by axial tension-tension cyclic fatigue tests. The schematics of FIGS. 9A and 9B show the axial displacements experienced by the stent shown in FIG. 5A during the fatigue tests, where cyclic loading is achieved by repeating these axial displacements. Table 1 below provides fatigue data for Zilver Vena™ stents that (a) are not treated; (b) are exposed to a tensile stress only prior to use/testing; and (c) are exposed to a compressive stress and a tensile stress prior to use/testing, as described herein. As can be observed, a medical device comprising a superelastic nickel-titanium alloy that is exposed to both a tensile stress and a compressive stress as described herein prior to testing/use exhibits a 117% improvement in fatigue endurance limit compared to the untreated device. As used in this disclosure, "fatigue endurance limit" refers to the amplitude of cyclic strain that may be applied to a sample without causing fatigue failure. Also revealed in the table is that a medical device exposed to just a tensile stress prior to testing/use exhibits (only) an 85% improvement in fatigue endurance limit. The data indicate that a medical device that undergoes the treatment method described herein may exhibit a fatigue endurance limit of greater than 0.9% (strain amplitude), as measured by axial tension-tension cyclic fatigue tests.

TABLE 1

Fatigue Endurance Limit of Zilver Vena ™ Stent

| Treatment (% strain induced) | Mean Strain (%) | Strain Amplitude (%) | Pass/Fail |
|---|---|---|---|
| none | 2.48 | 0.46 | 6 pass |
| | 2.45 | 0.49 | 2 pass/2 fail |
| 10.46 in tension | 2.57 | 0.85 | 5 pass |
| | 2.60 | 0.90 | 1 fail |
| 10.13 in compression and 10.46 in tension | 2.68 | 1.00 | 5 pass |
| | 2.80 | 1.10 | 2 fail |

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A method of treating a superelastic medical device to improve fatigue life, the method comprising:
    applying a compressive stress to a fatigue critical location of a medical device comprising a superelastic nickel-titanium alloy, the compressive stress inducing a compressive strain of greater than 9%;
    after inducing the compressive strain, releasing the compressive stress;
    applying a tensile stress to the fatigue critical location of the medical device, the tensile stress inducing a tensile strain of greater than 9%; and
    after inducing the tensile strain, releasing the tensile stress,
    wherein, after application and release of each of the compressive stress and the tensile stress, the fatigue critical location includes a non-zero amount of residual strain.

2. The method of claim 1, wherein the compressive stress is applied before the tensile stress is applied.

3. The method of claim 1, wherein the tensile stress is applied before the compressive stress is applied.

4. The method of claim 1, wherein the tensile stress and the compressive stress are applied by a method selected from the group consisting of radially compressing, radially expanding, bending, twisting, axially extending and/or axially compressing the medical device.

5. The method of claim 1, wherein the fatigue critical location is on a surface of the medical device.

6. The method of claim 1, wherein the compressive strain is at least about 10%.

7. The method of claim 1, wherein the tensile strain is at least about 10%.

8. The method of claim 1, wherein the fatigue critical location includes at least about 1% residual strain after application and release of each of the compressive stress and the tensile stress.

9. The method of claim 1, wherein the nickel-titanium alloy has an austenite finish temperature ($A_f$) less than body temperature, the medical device thereby being superelastic at body temperature.

10. The method of claim 9, wherein the austenite finish temperature ($A_f$) is less than room temperature, the medical device thereby being superelastic at room temperature.

11. The method of claim 1, wherein the medical device is an intraluminal device selected from the group consisting of: stent, filter, basket, plug, grasper, snare, and heart valve.

12. The method of claim 11, wherein the medical device comprises a stent configured to expand from a radially compressed configuration to a radially expanded configuration, the stent comprising an arrangement of interconnected struts, and
    wherein the fatigue critical location lies between adjacent interconnected struts.

13. The method of claim 12, wherein the tensile stress is applied by axially extending the stent.

14. The method of claim 12, wherein the compressive stress is applied by radially compressing the stent.

15. The method of claim 14, wherein the tensile stress is applied before the compressive stress,
    wherein, after applying the compressive stress, the stent is inserted into a sheath for delivery into a body vessel, deploying the stent in the body vessel, and
    releasing the compressive stress when the stent is deployed in the body vessel.

16. The method of claim 1, wherein the medical device exhibits a fatigue endurance limit of greater than 0.9% (strain amplitude).

17. The method of claim 1, further comprising, prior to applying the compressive stress or the tensile stress, exposing the medical device to a heat-setting treatment.

18. The method of claim 1, wherein the superelastic nickel-titanium alloy comprises from greater than 50 at. % to about 55 at. % nickel and from about 45 at. % to less than 50 at. % titanium.

19. The method of claim 18, wherein the superelastic nickel-titanium alloy includes one or more additional alloying elements.

20. The method of claim 1, wherein the medical device comprises a stent,
  wherein each of the tensile strain and the compressive strain is at least about 10%;
  wherein the tensile stress is applied by axially extending the stent before the compressive stress is applied,
  wherein the compressive stress is applied by radially compressing the stent,
  wherein, after applying the compressive stress, the stent is inserted into a sheath for delivery into a body vessel, deploying the stent in the body vessel, and
  releasing the compressive stress when the stent is deployed in the body vessel.

\* \* \* \* \*